United States Patent
Wiley et al.

(10) Patent No.: US 7,297,706 B2
(45) Date of Patent: Nov. 20, 2007

(54) CERTAIN GLYCINE DERIVATIVES AS FACTOR XA INHIBITORS FOR USE IN THE TREATMENT OF THROMBOTIC DISORDERS

(75) Inventors: Michael Robert Wiley, Indianapolis, IN (US); Daniel Jon Sall, Greenwood, IN (US); Christopher William Murray, Cambridge (GB); Stephen Clinton Young, Stockport (GB); Jolie Anne Bastian, Beech Grove, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/456,589

(22) Filed: Jul. 11, 2006

(65) Prior Publication Data

US 2007/0072869 A1  Mar. 29, 2007

Related U.S. Application Data

(62) Division of application No. 10/496,020, filed as application No. PCT/US02/36150 on Dec. 9, 2002, now Pat. No. 7,078,415.

(60) Provisional application No. 60/339,326, filed on Dec. 12, 2001.

(51) Int. Cl.
  *A61K 31/4375* (2006.01)
  *A61K 31/435* (2006.01)
  *C07D 211/10* (2006.01)

(52) U.S. Cl. ............ 514/316; 546/186; 546/187; 546/188

(58) Field of Classification Search ............... 514/316; 546/186, 187, 188
See application file for complete search history.

(56) References Cited

U.S. PATENT DOCUMENTS

| 6,262,069 | B1 | 7/2001 | Liebeschuetz et al. |
| 6,521,609 | B1 | 2/2003 | Doods et al. |
| 6,855,715 | B1* | 2/2005 | Liebeschuetz et al. ... 514/235.2 |
| 6,900,196 | B2 | 5/2005 | Liebeschuetz et al. |
| 2004/0254374 | A1 | 12/2004 | Jones et al. |
| 2005/0026928 | A1 | 2/2005 | Wiley et al. |

FOREIGN PATENT DOCUMENTS

| WO | WO 99/11657 | 3/1999 |
| WO | WO 99/11658 | 3/1999 |
| WO | WO 00/71493 | 11/2000 |
| WO | WO 00/76971 | 12/2000 |
| WO | WO 01/96323 | 12/2001 |

OTHER PUBLICATIONS

Jones, Stuart D, et al., Bioorganic & Medicinal Chemistry Letters 11 (2001) 733-736.

* cited by examiner

*Primary Examiner*—Rebecca Anderson
*Assistant Examiner*—Susannah Chung
(74) *Attorney, Agent, or Firm*—Thomas E. Jackson

(57) ABSTRACT

Compounds of formula (I)

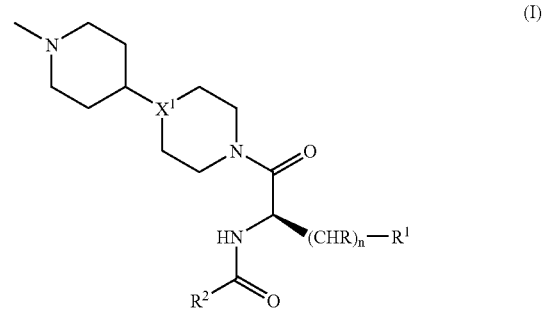

in which R, $R^1$, $R^2$, n and $X^1$ have the meanings given in the specification are Factor Xa inhibitors useful in the treatment of thrombotic disorders.

13 Claims, No Drawings

CERTAIN GLYCINE DERIVATIVES AS FACTOR XA INHIBITORS FOR USE IN THE TREATMENT OF THROMBOTIC DISORDERS

This application is a divisional application of application Ser. No. 10/496,020, granted as U.S. Pat. No. 7,078,415 on Jul. 18, 2006, the national stage of PCT/US02/36150, filed Dec. 9, 2002, and claims the benefit of U.S. provisional patent application Ser. No. 60/339,326 filed on Dec. 12, 2001.

The present invention relates to compounds useful as pharmaceuticals, to pharmaceutical compositions comprising the compounds, to a process for preparing the compounds, to intermediates useful in the preparation of the compounds, and to use of the compounds as pharmaceuticals.

Cardiovascular disease continues to present a major worldwide health problem, and is a common cause of serious illness and death.

One line of investigation being pursued by researchers in the search for new treatments for cardiovascular disease is based upon the hypothesis that an inhibitor of the serine protease, Factor Xa, may be useful as an anticoagulant agent in the treatment of thrombotic disease.

Inhibitors of Factor Xa are known. For example, WO 99/11657, WO 99/11658 and WO 00/76971 disclose certain compounds containing an aromatic group, a glycine residue that bears a cyclic group and a lipophilic group. WO 99/11657, which discloses compounds in which the aromatic group is an aminoisoquinoline group, also generically discloses aminoisoquinoline compounds containing a glycine residue that bears an acyclic group.

Surprisingly, compounds containing particular phenyl, indolyl or benzo[b]thiophene groups, a glycine residue bearing a heteroalkyl group and a 4-(1-methylpiperidin-4-yl)piperidin-1-yl or 4-(1-methylpiperidin-4-yl)piperazin-1-yl group have now been found that are selective Factor Xa inhibitors and have particularly advantageous properties.

Accordingly, the present invention provides a compound of formula (I)

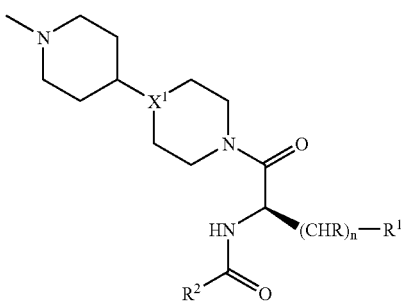

(I)

in which
X$^1$ represents CH or N;
n is 1 or 2;
each R represents hydrogen or methyl;
R$^1$ represents imidazol-1-yl or X$^a$R$^a$
in which
X$^a$ represents O, S or NR$^b$;
R$^a$ represents a hydrogen atom, a (1-4C)alkyl group, a phenyl group or a pyridyl group;
R$^b$ represents a hydrogen atom, a (1-4C)alkyl group or, together with R$^a$ and the nitrogen atom to which they are attached represents a saturated 4 to 6-membered ring which may contain, as a ring member, one of O, S and NR$^c$ in which R$^c$ represents hydrogen or (1-4C)alkyl; and
R$^2$ is selected from

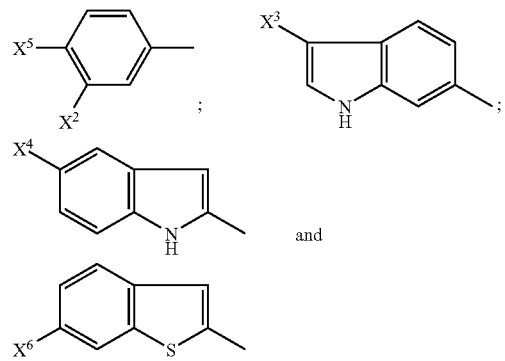

in which
X$^2$ represents a hydrogen atom, a halogen atom or an amino group;
X$^3$ represents a hydrogen atom, a methyl group, a fluorine atom, a chlorine atom or a bromine atom;
X$^4$ represents a hydrogen atom, a methyl group or a halogen atom;
X$^5$ represents a chlorine atom, a methoxy group or a methyl group; and
X$^6$ represents a hydrogen atom, a halogen atom or a methyl group;
or a pharmaceutically acceptable salt thereof.

Compounds of formula (I) have been found to be potent and selective inhibitors of the serine protease, Factor Xa, to have good anticoagulant activity in human plasma, to have good plasma exposure upon oral administration to mammals, and to possess particularly advantageous pharmacological and toxicological profiles of activity.

In the compounds of formula (I), preferably (CHR)$_n$ is selected from CH$_2$, CHCH$_3$ and CH$_2$CH$_2$.

R$^1$ preferably represents imidazol-1-yl, hydroxy, (1-4C)alkoxy, (1-4C)alkylthio, di(1-4C)alkylamino, phenylthio, pyridylthio, piperidin-1-yl or morpholino.

More preferably R$^1$ represents imidazol-1-yl, hydroxy, methoxy, methylthio, 2-propylthio, dimethylamino, phenylthio, pyrid-2-ylthio, piperidin-1-yl or morpholino.

Examples of particular values for (CHR)$_n$R$_1$ are imidazol-1-ylmethyl, hydroxymethyl, 1-hydroxyethyl, methoxymethyl, 1-methoxyethyl, methylthiomethyl, prop-2-ylthiomethyl, 2-methylthioethyl, N,N-dimethylaminomethyl, phenylthiomethyl, pyrid-2-ylthiomethyl, piperidin-1-ylmethyl and morpholinomethyl.

In the groups represented by R$^2$, X$^2$ preferably represents a hydrogen atom or a halogen atom.

More preferably X$^2$ represents a hydrogen atom or a fluorine atom;
X$^3$ represents a hydrogen atom, a fluorine atom, a chlorine atom or a methyl group;
X$^4$ represents a chlorine atom;
X$^5$ represents a chlorine atom or a methoxy group; and
X$^6$ represents a chlorine atom.

Particularly preferred values for R$^2$ are 4-chlorophenyl, 4-methoxyphenyl, 3-fluoro-4-methoxyphenyl, indol-6-yl, 3-methylindol-6-yl, 3-chloroindol-6-yl, 5-fluoroindol-2-yl, 5-chloroindol-2-yl or 6-chlorobenzo[b]thiophen-2-yl.

Especial mention may be made of compounds of formula (I) in which $R^2$ is 4-methoxyphenyl, indol-6-yl or 5-chloroindol-2-yl.

One particular value for $X^1$ is CH. Another is N.

As used herein, unless otherwise indicated, the term halogen atom includes fluorine, chlorine and bromine.

It will be appreciated that the compounds of formula (I) contain a center of asymmetry that has the (D) configuration. The (D) configuration refers to the configuration of the amino acids from which the compounds may be prepared. The compounds may therefore exist and be isolated in a mixture with the corresponding (L) isomer, such as a racemic mixture, or separately. Preferably the compounds are isolated substantially free of the (L) isomer.

It will also be appreciated that the compounds of formula (I) or their pharmaceutically acceptable salts may be isolated in the form of a solvate, and accordingly that any such solvate is included within the scope of the present invention.

The compounds of formula (I) and their pharmaceutically acceptable salts may be prepared by a process, which comprises (a) reacting a compound of formula (II)

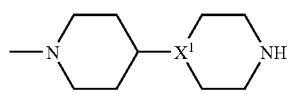
(II)

or a salt thereof, with a compound of formula (III)

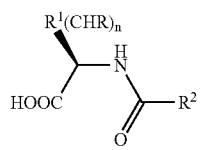
(III)

or a reactive derivative thereof; or (b) reacting a compound of formula (IV)

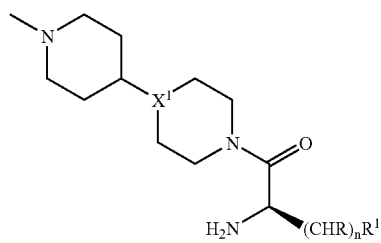
(IV)

or a salt thereof, with a compound of formula (V)

 (V)

or a salt or reactive derivative thereof;

followed, if a pharmaceutically acceptable salt is desired, by forming a pharmaceutically acceptable salt.

The reaction between a compound of formula (II) with a compound of formula (III) may conveniently be performed employing reagents and reaction conditions conventionally used for the formation of an amide bond. The reaction is conveniently carried out in the presence of a benzotriazole-based reagent such as 1-hydroxybenzotriazole or 1-hydroxy-7-azabenzotriazole and a dehydrating agent such as dicyclohexylcarbodiimide or 1-(3-dimethylaminopropyl)-3-ethylcarbodiimide, in an inert organic solvent such as dimethylformamide and/or methylene chloride. The reaction is conveniently conducted at a temperature of from 0 to 50° C., preferably at ambient temperature. If a salt of a compound of formula (II) is used, the reaction is conveniently performed in the additional presence of a base such as triethylamine. Other suitable reagents and solvents are known in the art, for example an acid halide, such as the chloride in the presence of a base, such as triethylamine.

The reaction between a compound of formula (IV) with a compound of formula (V) may conveniently be performed employing reagents and reaction conditions conventionally used for the formation of an amide bond. The reaction is conveniently carried out in the presence of a benzotriazole-based reagent such as 1-hydroxybenzotriazole or 1-hydroxy-7-azabenzotriazole and a dehydrating agent such as dicyclohexylcarbodiimide or 1-(3-dimethylaminopropyl)-3-ethylcarbodiimide, in an inert organic solvent such as dimethylformamide and/or methylene chloride. The reaction is conveniently conducted at a temperature of from 0 to 50° C., preferably at ambient temperature. If a salt of a compound of formula (IV) is used, the reaction is conveniently performed in the additional presence of a base such as triethylamine. Other suitable reagents and solvents are known in the art, for example an acid halide, such as p-anisoyl chloride in the presence of a base, such as triethylamine. Alternatively, the compound of formula (IV) may be reacted with a compound of formula (V) in the presence of diethylcyanophosphonate. This reaction is conveniently performed in an organic solvent such as dichloromethane in the presence of a base, such as triethylamine. The temperature is conveniently in the range of from −25 to 25° C.

The compound of formula (II) in which $X^1$ is CH is known, for example from WO 00/76971 at pages 163-164, and is named as 4-(1-methylpiperidin-4-yl)piperidine or 1-methyl-4,4'-bispiperidine.

The compound of formula (II) in which $X^1$ is N is referred to herein as 1-(1-methylpiperidin-4-yl)piperazine.

The compounds of formula (III) may be prepared by reacting a compound of formula (VI)

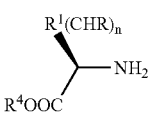
(VI)

in which $R^4$ represents a carboxyl protecting group, for example a (1-6C)alkyl group, such as methyl or ethyl, with a compound of formula (IV) to afford a compound of formula (VII)

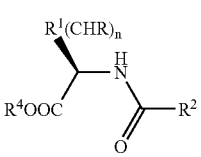
(VII)

followed by removing the protecting group.

The compounds of formula (IV) may be prepared by reacting a compound of formula (II) with a compound of formula (VIII)

(VIII)

in which $R^5$ represents an amino protecting group, such as t-butoxycarbonyl (Boc) to afford a compound of formula (IX)

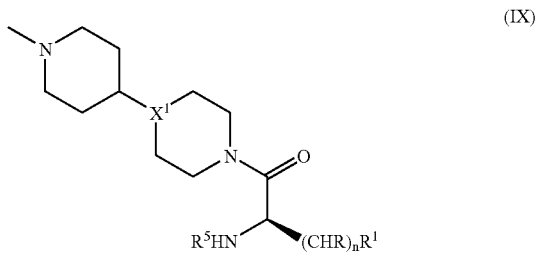

(IX)

followed by removing the protecting group.

The compounds of formulae (VI) and (VIII) are known or may be prepared using conventional methods for the preparation of amino acids protected on the carboxy or amino group. Particular preparations are also described in the Examples.

The compounds of formula (V) are well known.

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$-$C_6$ alkyl groups such as methyl, ethyl, t-butyl and t-amyl; aryl($C_1$-$C_4$)alkyl groups such as benzyl, 4-nitro-benzyl, 4-methoxybenzyl, 3,4-dimethoxybenzyl, 2,4-dimethoxy-benzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups include acyl groups, such as groups of formula RCO in which R represents $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$-$C_4$ alkyl and $C_1$-$C_4$ alkoxy.

Preferred amino protecting groups include benzyloxycarbonyl (CBz) and t-butoxycarbonyl (Boc).

Certain of the intermediates described herein, for example the compounds of formulae (III) and (IV), are believed to be novel and accordingly are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Viewed from this aspect the invention provides a pharmaceutical composition, which comprises the compound of formula (I) or a pharmaceutically acceptable salt thereof, together with a pharmaceutically acceptable diluent or carrier.

According to another aspect, the present invention provides the compound of formula (I) or a pharmaceutically acceptable salt thereof, for use in therapy.

According to another aspect, the present invention provides the use of the compound of formula (I) or a pharmaceutically acceptable salt thereof, for the manufacture of a medicament for the treatment of a thrombotic disorder.

According to another aspect, the present invention provides a method of treating a thrombotic disorder in a subject requiring treatment, which comprises administering an effective amount of a compound of formula (I) or a pharmaceutically acceptable salt thereof.

The subject may be a human or a non-human animal, such as a non-human mammal, for example a cat, dog, horse, cow or sheep.

The thrombotic disorder may be, for example, venous thrombosis, pulmonary embolism, arterial thrombosis, myocardial ischaemia, myocardial infarction or cerebral thrombosis. A particular indication is, for example, prophylaxis of post-operative venous thrombosis following high risk orthopedic surgery (such as hip or knee replacement), primary treatment of venous thrombosis, secondary prevention of ischemic cardiovascular complications following myocardial infarction (in combination with e.g. low dose aspirin), or prevention of embolic stroke in non-valvular atrial fibrillation. The compounds may also be used in accordance with the method of the invention in the treatment of acute vessel closure associated with thrombolytic therapy and restenosis, for example after transluminal coronary angioplasty or bypass grafting of the coronary or peripheral arteries, and in the maintenance of vascular access patency in long term hemodialysis patients.

The dosage of the compound of formula (I) will depend upon the nature and severity of the condition being treated, the administration route and the size and species of the subject. In general, quantities in the range of from 0.01 to 100 μM/kg bodyweight will be administered.

As used herein, the term "treatment" includes prophylactic use. The term "effective amount" refers to the amount of the compound of formula (I) that is effective to reduce or inhibit the development of the symptoms of the thrombotic disorder being treated.

The compound according to the invention may be administered alone or in combination with an anticoagulant having a different mode of action or with a thrombolytic agent.

The following Examples illustrate the invention.

Abbreviations used follow IUPAC-IUB nomenclature. Additional abbreviations are Boc, tertiary-butyloxycarbonyl; DCC, dicyclohexylcarbodiimide; DIEA, N,N-diisopropylethyl-amine; DMSO, dimethyl sulfoxide (perdeuterated if for NMR); DMF, dimethylformamide; EDCI, 1-(3-dimethylaminopropyl)-3-ethylcarbodiimide; ES-MS, electrospray mass spectrum; EtOAc, ethyl acetate; $Et_2O$, diethyl ether; HOAt, 1-hydroxy-7-aza-benzotriazole; HOBt, 1-hydroxy benzotriazole; HPLC, high pressure liquid chromatography; MeOH, methanol; SCX, strong cation exchange;

TEA, triethylamine; TFA, trifluoroacetic acid; and THF, tetrahydrofuran. Reagents were obtained from a variety of commercial sources.

The following abbreviations are used throughout: Abbreviations used follow IUPAC-IUB nomenclature. Additional abbreviations are Boc, tertiary-butyloxycarbonyl; CMA, chloroform: methanol: concentrated ammonium hydroxide (80:18:2); DEPC, diethyl cyanophosphonate. DCC, dicyclohexylcarbodiimide; DIEA, N,N-diisopropylethylamine; DMSO, dimethyl sulfoxide (perdeuterated if for NMR); DMF, dimethylformamide; EDCI, 1-[3-(dimethylamino) propyl]-3-ethylcarbodiimide hydrochloride; ES-MS, electrospray mass spectrum; EtOAc, ethyl acetate; $Et_2O$, diethyl ether; HOAt, 1-hydroxy-7-azabenzotriazole; HOBt, 1-hydroxybenzotriazole; HPLC, high pressure liquid chromatography; MeOH, methanol; SCX, strong cation exchange; TEA, triethylamine; TFA, trifluoroacetic acid; and THF, tetrahydrofuran. Reagents were obtained from a variety of commercial sources.

General Lactone Opening Methods

Method 1: In a manner similar to that described by L. N. Jungheim, et al.; *J. Med. Chem.* 1996, 39, 96-108, a 0° C. solution of N-Boc-D-serine β-lactone (1 eq; prepared according to Marinez, E. R.; Salmassian, E. K.; Lau, T. T.; Gutierrez, C. G. *J. Org. Chem.* 1996, 61, 3548-3550) in THF (0.3 M) is treated with a sodium thioalkoxide (1.1 eq). After stirring for 30 min, the reaction mixture is allowed to warm to room temperature and stir for an additional 2-3 h, before it is acidified with 10% aqueous sodium bisulfate solution. The aqueous layer is extracted with ethyl acetate twice, and the combined organic layers are dried over $Na_2SO_4$, filtered and concentrated in vacuo. The crude residue is purified by chromatography over silica gel, eluting with a mixture of 1 to 2% methanol in dichloro-methane with 0.5% acetic acid. The product-containing fractions are then combined and concentrated in vacuo.

Method 2: In a manner similar to that described by Ratemi, E. S.; Vederas, J. C. *Tetrahedron Lett.* 1994, 35, 7605-7608, a solution of an N-trimethylsilylamine (1.3 eq) in acetonitrile (0.3 M) is treated with a solution of N-Boc-D-serine β-lactone (1 eq) in acetonitrile (0.1 M). After stirring for 3 h, the reaction mixture is concentrated in vacuo. The crude residue is dissolved in 3:1 methanol/THF (0.05 to 0.1 M) and treated with 10% w/v aqueous potassium carbonate solution (approximately 25% of the organic solvent volume). After stirring for 1.5 h, the reaction mixture is concentrated in vacuo; and the resulting solid is triturated with dichloromethane containing a small amount of methanol. The organic filtrate is concentrated in vacuo to give the potassium salt of the acid, which is used without further purification.

General Coupling Methods

Method 1: A solution or suspension of an amine, amine hydrochloride salt or amine hydrobromide salt (1 eq, approximately 0.1 to 0.2 M) in THF, dichloromethane, or DMF (or a mixture of any of these solvents) is treated with either a carboxylic acid (approximately 1 eq) or a carboxylic acid potassium salt, either HOBt or HOAt (approximately 1 eq), either TEA or DIEA (0-5 eq), and either EDCI or DCC (approximately 1 eq). After stirring overnight at room temperature, the reaction mixture is washed with saturated aqueous sodium bicarbonate solution. The aqueous layer is extracted twice with ethyl acetate or dichloromethane. The combined organic layers are then dried with $MgSO_4$ or $Na_2SO_4$, filtered and concentrated in vacuo. If necessary, the product is purified by chromatography over silica gel, eluting with a gradient of 0% through 5 to 15% 2 N ammonia/methanol in dichloromethane. The product-containing fractions are then combined and concentrated in vacuo. Alternatively, the product can be purified by reverse phase HPLC on C-18 using a 5 to 95% gradient of acetonitrile in $H_2O$ with 0.01% HCl. The product-containing fractions are then combined and freeze-dried.

Method 2: To a stirring solution of an amine or amine hydrochloride salt (1 eq), triethylamine (1-3 eq), and a carboxylic acid (about 1.2 eq) in dichloromethane (0.2-0.5M) at 0° C., is slowly added diethyl cyanophosphonate (about 1.2 eq). After stirring overnight, the solvents are removed in vacuo and the residue is partitioned between an organic solvent such as ethyl acetate or dichloromethane and washed with saturated aq. $NaHCO_3$, followed by brine. The organic phase is then dried with $MgSO_4$ or $Na_2SO_4$, filtered and concentrated in vacuo. If necessary, the product is purified by chromatography over silica gel, eluting with a gradient of 0-10% 2 N ammonia/methanol in either dichloromethane or chloroform. The product-containing fractions are then combined and concentrated in vacuo.

Method 3: The amine or amine hydrochloride salt (1 eq) and triethylamine (1-3 eq) are dissolved in dichloromethane (0.1-0.5 M) and an acid chloride (about 1.2 eq) is added. After stirring overnight, the reaction mixture is quenched with saturated $NaHCO_3$ solution. The aqueous layer is extracted twice with dichloromethane, and the combined organic layers are dried over $Na_2SO_4$, filtered and concentrated in vacuo. If necessary, the product can be purified by chromatography over silica gel, eluting with a gradient of 0% through 5 to 10% 2 N ammonia/methanol in dichloromethane. The product-containing fractions are then combined and concentrated in vacuo. Alternatively, the crude product can be purified by reverse phase HPLC using a 5 to 95% gradient of 0.01% $HCl/H_2O$ in acetonitrile. The product-containing fractions are then combined and freeze-dried.

Method 4: A solution or suspension of an amine or amine hydrochloride salt (1 eq, approximately 0.2 M) in THF, dichloromethane, or DMF (or a mixture of any of these solvents) is treated with a carboxylic acid (approximately 1 eq), and either TEA or DIEA (0-3 eq) and mixed several minutes. Either HOBt or HOAt (approximately 1 eq) and either EDCI or DCC (approximately 1 eq) are separately stirred together in a solvent; and the resulting mixture is added to the other solution, or vice versa. After stirring overnight at room temperature, the solvents may be removed; and then the mixture is diluted with an organic solvent (such as ethyl acetate or dichloromethane) and washed with saturated aqueous sodium bicarbonate followed by brine. The organic solution is then dried with $MgSO_4$, filtered and concentrated in vacuo. When DCC is used as the coupling reagent, after stirring overnight at room temperature, the mixture may be filtered to remove dicyclohexyl urea, and then purified by SCX chromatography as described below.

If necessary, the product may be then purified by chromatography over silica gel, eluting with a gradient of 0% through 2 to 12% 2 N ammonia/methanol in dichloromethane or chloroform. The product-containing fractions are then combined and concentrated in vacuo.

General Deprotection Methods

Method 1 (t-butyl carbamate): A solution of the t-butyl carbamate (1 eq) in $CH_2Cl_2$ (0.2 M) is treated with anisole (5 eq) and TFA (20% by volume). After stirring 1 to 3 h at ambient temperature, the reaction mixture is concentrated in vacuo. The crude residue is purified by strong cation exchange (SCX) chromatography. The SCX column is washed with a 5% solution of acetic acid in methanol and the TFA salt is dissolved in methanol (possibly with a cosolvent such as dichloromethane) and loaded onto the SCX column. The column is then washed with methanol (possibly with a cosolvent such as dichloromethane) and then the free base is eluted from the column with a 2 N solution of ammonia or triethylamine in methanol (possibly with a cosolvent such as dichloromethane). The product containing fractions are then combined and concentrated in vacuo to give the product in the free base form.

Method 2 (t-butyl carbamate): HCl gas is bubbled into a solution of the t-butyl carbamate in anhydrous MeOH (0.1 M) for approximately 10 to 30 min, then the reaction mixture is concentrated in vacuo.

Method 3: A solution of the benzyl carbamate and 10% Pd/C (15% w/w) in anhydrous EtOH (0.1 M) is subjected to an atmosphere of $H_2$ at room temperature and pressure and allowed to stir overnight. The reaction mixture is filtered over diatomaceous earth, and the filtrate is concentrated in vacuo.

General HCl Salt Formation Methods

Method 1: The free base is dissolved in 0.2 N aqueous HCl (1-2 eq of HCl). The resulting solution is freeze-dried to give the amine hydrochloride salt.

Method 2: A solution of the free base in a small amount of dichloromethane is treated with 1.0-2.2 equivalents of 1 M HCl in ether. After stirring about 30 min, the reaction mixture is filtered; and the resulting solid is rinsed with ether and dried to give the amine hydrochloride salt.

Method 3: A solution of the free base in a small amount of MeOH is treated with a 0.5 M solution of ammonium chloride in MeOH (1 eq). The resulting solution is concentrated in vacuo to give the amine hydrochloride salt.

General Analytical HPLC Methods

Method 1: Vydac C18 (4.6×250 mm) or Symmetry (4.6×150 mm), elute with a linear gradient of 90/10 through 50/50 (0.1% TFA in water/0.1% TFA in acetonitrile) over 45 min, 1 mL/min, $\lambda$=214 nm.

Method 2: Xterra RP18 4.6×150 mm column, gradient of 10-50% $CH_3CN$ in $H_2O$ with 0.1% TFA, 1 mL/min, over 40 min, Waters 996 PDA and/or Sedex ELS detection.

Method 3: Xterra RP18 4.6×50 mm column, gradient of 2-50% $CH_3CN$ in $H_2O$ with 0.1% TFA, 1 mL/min, over 30 min, $\lambda$=214 nm.

Method 4: Xterra RP18 4.6×50 mm column, gradient of 2-70% $CH_3CN$ in $H_2O$ with 0.1% TFA, 1 mL/min, over 30 min, $\lambda$=214 nm.

Preparations of Amino Acid Intermediates

N-Boc-O-Methyl-D-threonine Methyl Ester

Prepared using methods similar to those described in Andurkar, S. V.; Stables, S. P.; Kohn. H. *Tetrahedron Asymm.*, 1998, 9(21), 3841-3854. To a solution of N-Boc-D-threonine (36.5 mmol) in acetonitrile (500 mL) protected from external light, is added $Ag_2O$ (182.5 mmol) and $CH_3I$ (365.0 mmol). After stirring for 3-4 days, the mixture is filtered through diatomaceous earth and concentrated in vacuo. The residue is then chromatographed over silica gel, eluting with a gradient of 0% ethyl acetate in hexanes through 100% ethyl acetate in hexanes. The product containing fractions are combined and concentrated to give 4.78 g (52.9%) of the title compound.

$^1$H NMR. Analysis for $C_{11}H_{21}NO_5$.0.1 $H_2O$: Calcd: C 52.41; H 8.40; N 5.56; Found: C 52.44; H 7.89; N 5.70.

N-Boc-O-Methyl-D-allo-threonine Methyl Ester

Prepared from N-Boc-D-allo-threonine using methods substantially equivalent to those described above for the preparation of N-Boc-O-methyl-D-threonine methyl ester. (70%).

$^1$H NMR. ES-MS m/z 248.0 (M+1)$^+$.

N-Boc-O-Methyl-D-threonine

To a solution of N-Boc-O-methyl-D-threonine methyl ester (8.09 mmol) in 1,4-dioxane (10 mL) is added a solution of LiOH (24.3 mmol) in water (20 mL). After stirring for 2-3 h, the solvents are removed in vacuo and the residue partitioned between water and ether. The aqueous layer is acidified with solid citric acid to approximately pH 3, then extracted with ethyl acetate. The ethyl acetate extract is washed with water, dried with $MgSO_4$, filtered and concentrated in vacuo to yield 1.70 g (90%) of the title compound.

$^1$H NMR. Analysis for $C_{10}H_{19}NO_5$.0.1 $H_2O$: Calcd: C 50.45; H 8.05; N 5.88; Found: C 50.67; H 8.01; N 5.73.

N-Boc-O-Methyl-D-allo-threonine

Prepared from N-Boc-O-methyl-D-allo-threonine methyl ester using methods substantially equivalent to those described above for the preparation of N-Boc-O-methyl-D-threonine (99%).

$^1$H NMR. Analysis for $C_{10}H_{19}NO_5$.0.14 $H_2O$: Calcd: C 50.05; H 7.98; N 5.84; Found: C 49.64; H 7.67; N 5.81.

N-Boc-D-allo-Threonine

Prepared from D-allo-threonine using methods substantially equivalent to those described in Shuman, R. T.; Ornstein, P. L.; Paschal, J. W.; Geselchen, P. D., *J. Org. Chem*, 1990, 55, 738-741.

$^1$H NMR. ES-MS m/z 218.2 (M−1)$^-$.

Preparation of Compounds of Formula (IX), $X^1$=CH 1-(N-Boc-D-Serinyl)-4-(1-methylpiperidin-4-yl) piperidine Prepared from Boc-D-serine and 4-(1-methylpiperidin-4-yl)piperidine dihydrobromide (WO 00/76971) using methods substantially equivalent to General Coupling Method 1.

$^1$H NMR. ES-MS, m/z 370.3 (M+1)$^+$. Analysis For $C_{19}H_{35}N_3O_4$.0.3.$H_2O$: Calcd: C 60.87; H 9.57; N 11.21; Found: C 60.87; H 9.37; N 11.19.

1-(N-Cbz-O-Methyl-D-serinyl)-4-(1-methylpiperidin-4-yl)-piperidine

Prepared from N-Cbz-O-methyl-D-serine (Andurkar, S. V.; Stables, J. P.; Kohn, H.; *Tetrahedron: Asymm*, 1998, 9 (21), 3841-3854) and 4-(1-methylpiperidin-4-yl)piperidine dihydrobromide using methods substantially equivalent to General Coupling Method 1.

$^1$H NMR. ES-MS, m/z 418.3 (M+1)$^+$. Analysis For $C_{23}H_{35}N_3O_4$.0.2 $H_2O$: Calcd: C 65.59; H 8.47; N 9.98. Found: C 65.61; H 8.57; N 9.65.

1-(N-Boc-D-Threoninyl)-4-(1-methylpiperidin-4-yl)piperidine

Prepared from Boc-D-threonine and 4-(1-methylpiperidin-4-yl)piperidine dihydrobromide using methods substantially equivalent to General Coupling Method 4.

ES-MS, m/z 384.3 (M+1)$^+$.

1-(N-Boc-D-allo-Threoninyl)-4-(1-methylpiperidin-4-yl)-piperidine

Prepared from N-Boc-D-allo-threonine and 4-(1-methylpiperidin-4-yl)piperidine dihydrobromide using methods substantially equivalent to General Coupling Method 1.

$^1$H NMR. ES-MS, m/z 384.5 (M+1)$^+$. Analysis for $C_{20}H_{37}N_3O_4 \cdot 0.2\ H_2O$: Calcd: C 60.73; H 9.43; N 10.62; Found: C 60.54; H 9.54; N 11.75.

1-(N-Boc-O-Methyl-D-threoninyl)-4-(1-methylpiperidin-4-yl)-piperidine

Prepared from N-Boc-O-methyl-D-threonine and 4-(1-methylpiperidin-4-yl)piperidine dihydrobromide using methods substantially equivalent to General Coupling Method 4.

$^1$H NMR. ES-MS, m/z 398.4 (M+1)$^+$. Analysis for $C_{21}H_{39}N_3O_4 \cdot H_2O$: Calcd: C 60.69; H 9.95; N 10.11; Found: C 60.55; H 9.55; N 11.21.

1-(N-Boc-D-Methioninyl)-4-(1-methylpiperidin-4-yl)-piperidine

Prepared from N-Boc-D-methionine and 4-(1-methyl-piperidin-4-yl)piperidinedihydrobromide using methods substantially equivalent to General Coupling Method 1.

$^1$H NMR. ES-MS, m/z 414.3 (M+1)$^+$. Analysis for $C_{21}H_{39}N_3O_3S \cdot 0.3\ H_2O$: Calcd: C 57.00; H 8.88; N 9.50; Found: C 57.34; H 8.89; N 8.81.

1-(N-Boc-S-Phenyl-D-cysteinyl)-4-(1-methylpiperidin-4-yl)-piperidine

Prepared from N-Boc-S-phenyl-D-cysteine (L. N. Jungheim, et al.; *J. Med. Chem.* 1996, 39, 96-108) and 4-(1-methylpiperidin-4-yl)piperidine dihydrobromide using methods substantially equivalent to General Coupling Method 1.

$^1$H NMR. ES-MS, m/z 462.3 (M+1)$^+$. Analysis for $C_{25}H_{39}N_3O_3S \cdot 1.2\ H_2O$: Calcd: C 62.13; H 8.63; N 8.70. Found: C 62.05; H 8.32; N 8.75.

1-[N-Boc-S-(2-Pyridyl)-D-cysteinyl]-4-(1-methylpiperidin-4-yl) piperidine

Prepared from N-Boc-S-(2-pyridyl)-D-cysteine (L. N. Jungheim, et al.; *J. Med. Chem.* 1996, 39, 96-108) and 4-(1-methylpiperidin-4-yl)piperidine dihydrobromide using methods substantially equivalent to General Coupling Method 1.

$^1$H NMR. ES-MS, m/z 463.3 (M+1)$^+$. Analysis for $C_{24}H_{38}N_4O_3S \cdot 0.7\ H_2O$: Calcd: C 60.65; H 8.36; N 11.79; Found: C 60.95; H 8.02; N 11.07.

1-[N-Boc-S-(2-Propyl)-D-cysteinyl]-4-(1-methylpiperidin-4-yl)piperidine

Prepared from N-Boc-S-(2-propyl)-D-cysteine and 4-(1-methylpiperidin-4-yl)piperidine dihydrobromide using methods substantially equivalent to General Coupling Method 1. N-Boc-S-(2-propyl)-D-cysteine is prepared from Boc-D-serine β-lactone and sodium 2-propanethiolate using methods substantially equivalent to General Lactone Opening Method 1.

$^1$H NMR. ES-MS, m/z 428.3 (M+1)$^+$. Analysis for $C_{22}H_{41}N_3O_3S \cdot H_2O$: Calcd: C 59.29; H 9.73; N 9.43; Found: C 58.95; H 9.38; N 9.21.

1-(N-Boc-S-Methyl-D-cysteinyl)-4-(1-methylpiperidin-4-yl)-piperidine

Prepared from N-Boc-S-methyl-D-cysteine and 4-(1-methylpiperidin-4-yl)piperidine dihydrobromide using methods substantially equivalent to General Coupling Method 1. N-Boc-S-methyl-D-cysteine is prepared from Boc-D-serine β-lactone and sodium thiomethoxide using methods substantially equivalent to General Lactone Opening Method 1.

$^1$H NMR. ES-MS, m/z 400.3 (M+1)$^+$. Analysis for $C_{20}H_{37}N_3O_3S \cdot 1.2\ H_2O$: Calcd: C 57.03; H 9.43; N 9.98; Found: C 57.03; H 8.85; N 9.92.

1-[N-Boc-β-(4-Morpholinyl)-D-alaninyl]-4-(1-methylpiperidin-4-yl)piperidine

Prepared from N-Boc-β-(4-morpholinyl)-D-alanine potassium salt and 4-(1-methylpiperidin-4-yl)piperidine dihydrobromide using methods substantially equivalent to General Coupling Method 1. N-Boc-β-(4-morpholinyl)-D-alanine potassium salt is prepared from Boc-D-serine β-lactone and N-trimethylsilylmorpholine using methods substantially equivalent to General Lactone Opening Method 2.

$^1$H NMR. ES-MS, m/z 439.3 (M+1)$^+$.

1-(N-Boc-β-Dimethylamino-D-alaninyl)-4-(1-methylpiperidin-4-yl)piperidine

Prepared from N-Boc-β-dimethylamino-D-alanine, potassium salt and 4-(1-methylpiperidin-4-yl)piperidine dihydrobromide using methods substantially equivalent to General Coupling Method 1. N-Boc-β-dimethylamino-D-alanine potassium salt is prepared from Boc-D-serine β-lactone and N,N-dimethyltrimethylsilylamine using methods substantially equivalent to General Lactone Opening Method 2.

$^1$H NMR. ES-MS, m/z 397.3 (M+1)$^+$. Analysis for $C_{21}H_{40}N_4O_3$: Calcd: C 63.60; H 10.17; N 14.13; Found: C 63.84; H 9.82; N 13.27.

1-[N-Boc-β-(1-Imidazolyl)-D-alaninyl]-4-(1-methylpiperidin-4-yl)piperidine

Prepared from N-Boc-β-(1-imidazolyl)-D-alanine potassium salt and 4-(1-methylpiperidin-4-yl)piperidine dihydrobromide using methods substantially equivalent to General Coupling Method 1. N-Boc-β-(1-imidazolyl)-D-alanine potassium salt is prepared from Boc-D-serine β-lactone and 1-(trimethylsilyl)imidazole using methods substantially equivalent to General Lactone Opening Method 2.

$^1$H NMR. ES-MS, m/z 420.3 (M+1)$^+$. Analysis for $C_{22}H_{37}N_5O_3 \cdot 0.4\ H_2O$: Calcd: C 61.91; H 8.93; N 16.41; Found: C 62.01; H 8.49; N 15.80.

1-[N-Boc-β-(1-Piperidinyl)-D-alaninyl]-4-(1-methylpiperidin-4-yl)piperidine

Prepared from N-Boc-β-(1-piperidinyl)-D-alanine potassium salt and 4-(1-methylpiperidin-4-yl)piperidine dihydrobromide using methods substantially equivalent to General Coupling Method 1. N-Boc-β-(1-piperidinyl)-D-alanine potassium salt is prepared from Boc-D-serine β-lactone and 1-(trimethylsilyl)piperidine using methods substantially equivalent to General Lactone Opening Method 2.
$^1$H NMR. ES-MS, m/z 437.4 (M+1)$^+$.

Preparation of Compounds of Formula (IV), $X^1$=CH

1-(D-Serinyl)-4-(1-methylpiperidin-4-yl)piperidine Dihydrochloride

Prepared from 1-(N-Boc-D-serinyl)-4-(1-methylpiperidin-4-yl)piperidine using methods substantially equivalent to those described in General Deprotection Method 2.
$^1$H NMR. ES-MS, m/z 270.2 (M+1)$^+$. Analysis for $C_{14}H_{27}N_3O_2$.2.0 HCl.2.8 H$_2$O: Calcd: C 42.81; H 8.88; N 10.70. Found: C 43.15; H 9.13; N 10.13.

1-(O-Methyl-D-serinyl)-4-(1-methylpiperidin-4-yl)piperidine

Prepared from 1-(N-Cbz-O-methyl-D-serinyl)-4-(1-methyl-piperidin-4-yl)piperidine using methods substantially equivalent to those described in General Deprotection Method 3.
$^1$H NMR. ES-MS, m/z 284.2 (M+1)$^+$. Analysis for $C_{15}H_{29}N_3O_2$.0.1 $C_2H_5OH$.0.7 H$_2$O: Calcd: C 60.73; H 10.39; N 13.98; Found: C 60.57; H 9.89; N 13.73.

1-(D-Threoninyl)-4-(1-methylpiperidin-4-yl)piperidine

Prepared from 1-(N-Boc-D-threoninyl)-4-(1-methyl-piperidin-4-yl)piperidine using methods substantially equivalent to those described in General Deprotection Method 1. No data.

1-(D-allo-Threoninyl)-4-(1-methylpiperidin-4-yl)piperidine hydrochloride

Prepared from 1-(N-Boc-D-allo-threoninyl)-4-(1-methyl-piperidin-4-yl)piperidine using methods substantially equivalent to those described in General Deprotection Method 2.
$^1$H NMR. ES-MS, m/z 284.5 (M+1)$^+$. Analysis For $C_{15}H_{29}N_3O_2$.2.3 HCl.2.4 H$_2$O: Calcd: C 43.89; H 8.86; N 10.24; Cl 19.87; Found: C 43.46; H 8.70; N 10.67; Cl 19.61.

1-(O-Methyl-D-threoninyl)-4-(1-methylpiperidin-4-yl)-piperidine

Prepared from 1-(N-Boc-O-methyl-D-threoninyl)-4-(1-methylpiperidin-4-yl)piperidine using methods substantially equivalent to those described in General Deprotection Method 1.
ES-MS, m/z 298.1 (M+1)$^+$.

1-(D-Methioninyl)-4-(1-methylpiperidin-4-yl)piperidine

Prepared from 1-(N-Boc-D-methioninyl)-4-(1-methyl-piperidin-4-yl)piperidine using methods substantially equivalent to those described in General Deprotection Method 1.
$^1$H NMR. ES-MS, m/z 314.2 (M+1)$^+$.

1-(S-Phenyl-D-cysteinyl)-4-(1-methylpiperidin-4-yl)-piperidine Dihydrochloride Prepared from 1-(N-Boc-S-phenyl-D-cysteinyl)-4-(1-methylpiperidin-4-yl)piperidine using methods substantially equivalent to those described in General Deprotection Method 2.
$^1$H NMR. ES-MS, m/z 362.2 (M+1)$^+$. Analysis for $C_{20}H_{31}N_3OS$.1.7 HCl.1.7 H$_2$O: Calcd: C 52.89; H 8.01; N 9.25; Found: C 52.96; H 8.41; N 9.23.

1-[S-(2-Pyridyl)-D-cysteinyl]-4-(1-methylpiperidin-4-yl)-piperidine Dihydrochloride Prepared from 1-[N-Boc-S-(2-pyridyl)-D-cysteinyl]-4-(1-methylpiperidin-4-yl)piperidine using methods substantially equivalent to those described in General Deprotection Method 2.
$^1$H NMR. ES-MS, m/z 363.2 (M+1)$^+$. Analysis for $C_{19}H_{30}N_4OS$.1.9 HCl.5.0 H$_2$O: Calcd: C 43.73; H 8.09; N 10.74. Found: C 43.67; H 8.14; N 10.70.

1-[S-(2-Propyl)-D-cysteinyl]-4-(1-methylpiperidin-4-yl)-piperidine Dihydrochloride Prepared from 1-[N-Boc-S-(2-propyl)-D-cysteinyl-4-(1-methylpiperidin-4-yl)piperidine using methods substantially equivalent to those described in General Deprotection Method 2.
$^1$H NMR. ES-MS, m/z 328.2 (M+1)$^+$. Analysis for $C_{17}H_{33}N_3OS$.1.7 HCl.1.9 H$_2$O: Calcd: C 48.18; H 9.16; N 9.92; Found: C 48.18; H 9.47; N 9.82.

1-(S-Methyl-D-cysteinyl)-4-(1-methylpiperidin-4-yl)-piperidine Dihydrochloride Prepared from 1-(N-Boc-S-methyl-D-cysteinyl)-4-(1-methylpiperidin-4-yl)piperidine using methods substantially equivalent to those described in General Deprotection Method 2.
$^1$H NMR. ES-MS, m/z 300.2 (M+1)$^+$. Analysis For $C_{15}H_{29}N_3OS$.1.8 HCl.1.8 H$_2$O: Calcd: C 45.32; H 8.72; N 10.57. Found: C 45.38; H 9.07; N 10.41.

1-[β-(4-Morpholinyl)-D-alaninyl]-4-(1-methylpiperidin-4-yl)-piperidine Trihydrochloride Prepared from 1-[N-Boc-β-(4-morpholinyl)-D-alaninyl]-4-(1-methylpiperidin-4-yl)piperidine using methods substantially equivalent to those described in General Deprotection Method 2.
$^1$H NMR. ES-MS, m/z 339.3 (M+1)$^+$. Analysis for $C_{18}H_{34}N_4O_2$.3.0 HCl.1.3 H$_2$O: Calcd: C 45.87; H 8.47; N 11.89; Found: C 45.80; H 8.08; N 11.84.

1-[β-Dimethylamino-D-alaninyl]-4-(1-methylpiperidin-4-yl)-piperidine Hydrochloride Prepared from 1-[N-Boc-β-dimethylamino-D-alaninyl]-4-(1-methylpiperidin-4-yl)piperidine using methods substantially equivalent to those described in General Deprotection Method 2.
$^1$H NMR. ES-MS, m/z 297.3 (M+1)$^+$.

1-[β-(1-Imidazolyl)-D-alaninyl]-4-(1-methylpiperidin-4-yl)-piperidine Hydrochloride Prepared from 1-[N-Boc-β-(1-Imidazolyl)-D-alaninyl]-4-(1-methylpiperidin-4-yl)piperidine using methods substantially equivalent to those described in General Deprotection Method 2.

$^1$H NMR. ES-MS, m/z 320.2 (M+1)$^+$.

1-[β-(1-Piperidinyl)-D-alaninyl]-4-(1-methylpiperidin-4-yl)-piperidine Hydrochloride Prepared from 1-[N-Boc-β-(1-piperidinyl)-D-alaninyl]-4-(1-methylpiperidin-4-yl)piperidine using methods substantially equivalent to those described in General Deprotection Method 2.

$^1$H NMR. ES-MS, m/z 337.3 (M+1)$^+$.

EXAMPLES, X$^1$=CH

Example 1

1-[N-(Indole-6-carbonyl)-D-serinyl]-4-(1-methylpiperidin-4-yl)piperidine Hydrochloride Prepared from 1-(D-serinyl)-4-(1-methylpiperidin-4-yl)-piperidine and indole-6-carboxylic acid using methods substantially equivalent to General Coupling 4. The HCl salt is prepared following General Salt Formation Method 2.

$^1$H NMR. ES-MS, m/z 413.2 (M+1)$^+$; 411.2 (M−1)$^−$. Analysis for $C_{23}H_{32}N_4O_3 \cdot 1.2$ HCl$\cdot 1.6$ H$_2$O: Calcd: C 56.95; H 7.56; N 11.55; Cl 8.77; Found: C 57.23; H 7.57; N 11.15; Cl 8.74. Analytical HPLC (Method 1): >99%, $t_r$=14.1 min.

Example 2

1-[N-(5-Chloroindole-2-carbonyl)-D-serinyl]-4-(1-methyl-piperidin-4-yl)piperidine Hydrochloride Prepared from 1-(D-serinyl)-4-(1-methylpiperidin-4-yl)-piperidine dihydrochloride and 5-chloroindole-2-carboxylic acid using methods substantially equivalent to General Coupling Method 1. The HCl salt is prepared following General Salt Formation Method 1.

$^1$H NMR. ES-MS, m/z 447.2 (M+1)$^+$. Analysis for $C_{23}H_{31}N_4O_3Cl \cdot 1.1$ HCl$\cdot 1.6$ H$_2$O: Calcd: C 53.54; H 6.90; N 10.86; Cl 14.43; Found: C 53.61; H 6.44; N 10.82; Cl 14.09. Analytical HPLC (Method 4): >99%, $t_r$=12.1 min.

Example 3

1-[N-(3-Chloroindole-6-carbonyl)-D-serinyl]-4-(1-methyl-piperidin-4-yl)piperidine Hydrochloride Prepared from 1-(D-serinyl)-4-(1-methylpiperidin-4-yl)-piperidine dihydrochloride and 3-chloroindole-6-carboxylic acid using methods substantially equivalent to General Coupling Method 1. The HCl salt is prepared following General Salt Formation Method 1.

$^1$H NMR. ES-MS, m/z 447.2 (M+1)$^+$. Analysis for $C_{23}H_{31}N_4O_3Cl$ 1.1 HCl 1.9 H$_2$O: Calcd: C 52.99; H 6.94; N 10.75; Cl 14.28. Found: C 53.00; H 6.60; N 11.05; Cl 13.94. Analytical HPLC (Method 4): >99%, $t_r$=11.5 min.

Example 4

1-[N-(6-Chlorobenzo[b]thiophene-2-carbonyl)-D-serinyl]-4-(1-methylpiperidin-4-yl)piperidine Hydrochloride Prepared from 1-(D-serinyl)-4-(1-methylpiperidin-4-yl)-piperidine dihydrochloride and 6-chlorobenzo[b]thiophene-2-carboxylic acid using methods substantially equivalent to General Coupling Method 1. The HCl salt is prepared following General Salt Formation Method 1.

$^1$H NMR. ES-MS, m/z 464.2 (M+1)$^+$. Analysis for $C_{23}H_{30}N_3O_3SCl \cdot 1.3$ HCl$\cdot 0.6$ H$_2$O: Calcd: C 52.90; H 6.27; N 8.05; Cl 15.65; Found: C 52.94; H 6.27; N 8.08; Cl 15.48. Analytical HPLC (Method 3): >99%, $t_r$=19.9 min.

Example 5

1-[N-(Indole-6-carbonyl)-O-methyl-D-serinyl]-4-(1-methyl-piperidin-4-yl)piperidine Hydrochloride Prepared from 1-(O-methyl-D-serinyl)-4-(1-methyl-piperidin-4-yl)piperidine and indole-6-carboxylic acid using methods substantially equivalent to General Coupling Method 1. The HCl salt is prepared following General Salt Formation Method 1.

$^1$H NMR. ES-MS, m/z 427.3 (M+1)$^+$. Analysis for $C_{24}H_{34}N_4O_3 \cdot 1.0$ HCl$\cdot 1.8$ H$_2$O: Calcd: C 58.18; H 7.85; N 11.31; Cl 7.16; Found: C 58.20; H 7.89; N 11.38; Cl 7.12. Analytical HPLC (Method 3): >98%, $t_r$=15.9 min.

Example 6

1-[N-(Indole-6-carbonyl)-D-threoninyl]-4-(1-methyl-piperidin-4-yl)piperidine Hydrochloride Prepared from 1-(D-threoninyl)-4-(1-methylpiperidin-4-yl)piperidine and indole-6-carboxylic acid using methods substantially equivalent to General Coupling 4. The HCl salt is prepared following General Salt Formation Method 2.

$^1$H NMR. ES-MS, m/z 427.4 (M+1)$^+$; 425.3 (M−1)$^−$. Analysis for $C_{24}H_{34}N_4O_3 \cdot 0.85$ HCl$\cdot 1.4$ H$_2$O: Calcd: C 58.17; H 7.49; N 11.31; Cl 6.08; Found: C 58.53; H 7.94; N 10.77; Cl 6.46. Analytical HPLC (Method 1): 98%, $t_r$=15.2 min.

Example 7

1-[N-(Indole-6-carbonyl)-D-allo-threoninyl]-4-(1-methyl-piperidin-4-yl)piperidine Hydrochloride Prepared from 1-(D-allo-threoninyl)-4-(1-methyl-piperidin-4-yl)piperidine and indole-6-carboxylic acid using methods substantially equivalent to General Coupling Method 1. The HCl salt is prepared following General Salt Formation Method 2.

$^1$H NMR. ES-MS, m/z 427.5 (M+1)$^+$; 425.5 (M−1)$^−$. Analysis for $C_{24}H_{34}N_4O_3 \cdot 1.7$ HCl$\cdot 4.0$ H$_2$O: Calcd: C 51.42; H 7.86; N 10.00; Cl 10.75; Found: C 51.04; H 8.11; N 12.20; Cl 10.71. Analytical HPLC (Method 1): >98%, $t_r$=13.3 min.

Example 8

1-[N-(5-Chloroindole-2-carbonyl)-D-allo-threoninyl]-4-(1-methylpiperidin-4-yl)piperidine Hydrochloride Prepared from 1-(D-allo-threoninyl)-4-(1-methyl-piperidin-4-yl)piperidine hydrochloride and 5-chloroindole-2-carboxylic acid using methods substantially equivalent to General Coupling Method 1. The HCl salt is prepared following Salt Formation Method 2.

$^1$H NMR. ES-MS, m/z 461.5 (M+1)$^+$; 459.4 (M−1)$^−$. Analysis for $C_{24}H_{37}ClN_4O_3$·0.95 HCl·1.0 H$_2$O: Calcd: C 54.60; H 6.68; N 10.61; Cl 13.10; Found: C 55.15; H 6.78; N 10.68; Cl 13.42. Analytical HPLC (Method 1): >98%, $t_r$=22.2 min.

Example 9

1-[N-(Indole-6-carbonyl)-O-methyl-D-threoninyl]-4-(1-methyl-piperidin-4-yl)piperidine Hydrochloride Prepared from 1-(O-methyl-D-threoninyl)-4-(1-methyl-piperidin-4-yl)piperidine and indole-6-carboxylic acid using methods substantially equivalent to General Coupling Method 2. The HCl salt is prepared following General Salt Formation Method 2.

$^1$H NMR. ES-MS, m/z 441.5 (M+1)$^+$; 439.5 (M−1)$^−$. Analysis for $C_{25}H_{36}N_4O_3$·1.6 HCl·1.7 H$_2$O: Calcd: C 56.70; H 7.80; N 10.58; Cl 10.71; Found: C 56.81; H 8.18; N 10.17; Cl 10.77. Analytical HPLC (Method 1): >98%, $t_r$=18.8 min.

Example 10

1-[N-(4-Methoxybenzoyl)-O-methyl-D-threoninyl]-4-(1-methyl-piperidin-4-yl)piperidine Hydrochloride Prepared from 1-(O-methyl-D-threoninyl)-4-(1-methyl-piperidin-4-yl)piperidine and 4-methoxybenzoic acid using methods substantially equivalent to General Coupling Method 2. The HCl salt is prepared following General Salt Formation Method 2.

$^1$H NMR. ES-MS, m/z 432.5 (M+1)$^+$; 430.5 (M−1)$^−$. Analysis for $C_{24}H_{37}N_3O_4$·1.5 HCl·3.5 H$_2$O: Calcd: C 52.48; H 8.35; N 7.65; Cl 9.68; Found: C 52.26; H 8.24; N 7.62; Cl 9.77. Analytical HPLC (Method 1): >99%, $t_r$=17.4 min.

Example 11

1-[N-(Indole-6-carbonyl)-D-methioninyl]-4-(1-methyl-piperidin-4-yl)piperidine Hydrochloride Prepared from 1-(D-methioninyl)-4-(1-methylpiperidin-4-yl)piperidine and indole-6-carboxylic acid using methods substantially equivalent to General Coupling 4. The HCl salt is prepared following General Salt Formation Method 1.

$^1$H NMR. ES-MS, m/z 457.3 (M+1)$^+$; 455.4 (M−1)$^−$. Analysis for $C_{25}H_{36}N_4O_2$·1.4 HCl·0.75 H$_2$O: Calcd: C 58.88; H 7.84; N 10.99; Cl 9.73; Found: C 58.49; H 7.48; N 10.86; Cl 9.57. Analytical HPLC (Method 1): >93%, $t_r$=22.4 min.

Example 12

1-[N-(4-Methoxybenzoyl)-D-methioninyl]-4-(1-methylpiperidin-4-yl)piperidine Hydrochloride Prepared from 1-(D-methioninyl)-4-(1-methylpiperidin-4-yl)piperidine hydrochloride and 4-methoxybenzoic acid using methods substantially equivalent to General Coupling Method 4. The HCl salt is prepared following General Salt Formation Method 2.

$^1$H NMR. FD+, m/z 447.4 (M+1)$^+$. Analysis For $C_{24}H_{37}N_3O_3S$·1.1 HCl·0.9 H$_2$O: Calcd: C 56.11; H 7.69; N 8.18; Cl 6.2; Found: C 56.56; H 7.77; N 8.27; Cl 6.43. Analytical HPLC (Method 1): 98%, $t_r$=19.9 min.

Example 13

1-[N-(Indole-6-carbonyl)-S-phenyl-D-cysteinyl]-4-(1-methyl-piperidin-4-yl)piperidine Hydrochloride Prepared from 1-(S-phenyl-D-cysteinyl)-4-(1-methyl-piperidin-4-yl)piperidine and indole-6-carboxylic acid using methods substantially equivalent to General Coupling Method 1. The HCl salt is prepared following General Salt Formation Method 3.

$^1$H NMR. ES-MS, m/z 505.3 (M+1)$^+$. Analysis for $C_{29}H_{36}N_4O_2S$·1.0 HCl·0.6 H$_2$O: Calcd: C 63.10; H 6.98; N 10.15; Cl 6.42; Found: C 63.14; H 6.94; N 10.06; Cl 6.23. Analytical HPLC (Method 2): >97%, $t_r$=27.4 min.

Example 14

1-[N-(Indole-6-carbonyl)-S-(2-pyridyl)-D-cysteinyl]-4-(1-methylpiperidin-4-yl)piperidine Hydrochloride Prepared from 1-[S-(2-pyridyl)-D-cysteinyl]-4-(1-methylpiperidin-4-yl)piperidine and indole-6-carboxylic acid using methods substantially equivalent to General Coupling Method 1. The HCl salt is prepared following General Salt Formation Method 1.

$^1$H NMR. ES-MS, m/z 506.3 (M+1)$^+$. Analysis for $C_{28}H_{35}N_5O_2S$·1.2 HCl·1.4 H$_2$O: Calcd: C 58.52; H 6.84; N 12.19; Cl 7.40; Found: C 58.61; H 6.64; N 12.06; Cl 7.24. Analytical HPLC (Method 4): >99%, $t_r$=12.1 min.

Example 15

1-[N-(Indole-6-carbonyl)-S-(2-propyl)-D-cysteinyl]-4-(1-methylpiperidin-4-yl)piperidine Hydrochloride Prepared from 1-[S-(2-propyl)-D-cysteinyl]-4-(1-methyl-piperidin-4-yl)piperidine and indole-6-carboxylic acid using methods substantially equivalent to General Coupling Method 1. The HCl salt is prepared following General Salt Formation Method 1.

$^1$H NMR. ES-MS, m/z 471.3 (M+1)$^+$. Analysis for $C_{26}H_{38}N_4O_2S$·1.2 HCl·1.0 H$_2$O: Calcd: C 58.65; H 7.80; N 10.52; Cl 7.99; Found: C 58.65; H 7.68; N 10.49; Cl 7.80. Analytical HPLC (Method 4): >98%, $t_r$=12.9 min.

Example 16

1-[N-(Indole-6-carbonyl)-S-methyl-D-cysteinyl]-4-(1-methyl-piperidin-4-yl)piperidine Hydrochloride Prepared from 1-(S-methyl-D-cysteinyl)-4-(1-methyl-piperidin-4-yl)piperidine and indole-6-carboxylic acid using methods substantially equivalent to General Coupling Method 1. The HCl salt is prepared following General Salt Formation Method 3.

$^1$H NMR. ES-MS, m/z 443.2 (M+1)$^+$. Analysis for $C_{24}H_{34}N_4O_2S$·1.0 HCl·0.8 H$_2$O: Calcd: C 58.41; H 7.48; N 11.35; Cl 7.18; Found: C 58.33; H 7.31; N 11.14; Cl 7.06. Analytical HPLC (Method 2): >98%, $t_r$=18.7 min.

Example 17

1-[N-(5-Chloroindole-2-carbonyl)-S-methyl-D-cysteinyl]-4-(1-methylpiperidin-4-yl)piperidine Hydrochloride

Prepared from 1-(S-methyl-D-cysteinyl)-4-(1-methyl-piperidin-4-yl)piperidine and 5-chloroindole-2-carboxylic acid using methods substantially equivalent to General Coupling Method 1. The HCl salt is prepared following General Salt Formation Method 1.

$^1$H NMR. ES-MS, m/z 477.2 (M+1)$^+$. Analysis for $C_{24}H_{33}N_4O_2SCl \cdot 1.0$ HCl $\cdot 0.8$ H$_2$O: Calcd: C 54.60; H 6.80; N 10.61; Cl 13.43; Found: C 54.70; H 6.60; N 10.49; Cl 13.30. Analytical HPLC (Method 3): >92%, $t_r$=22.2 min.

Example 18

1-[N-(6-Chlorobenzo[b]thiophene-2-carbonyl)-S-methyl-D-cysteinyl]-4-(1-methylpiperidin-4-yl)piperidine Hydrochloride

Prepared from 1-(S-methyl-D-cysteinyl)-4-(1-methyl-piperidin-4-yl)piperidine and 6-chlorobenzo[b]thiophene-2-carboxylic acid using methods substantially equivalent to General Coupling Method 1. The HCl salt is prepared following General Salt Formation Method 1.

$^1$H NMR. ES-MS, m/z 494.2 (M+1)$^+$. Analysis for $C_{24}H_{32}N_3O_2S_2Cl \cdot 1.0$ HCl $\cdot 0.8$ H$_2$O: Calcd: C 52.89; H 6.40; N 7.71; Cl 13.01; Found: C 52.97; H 6.31; N 7.88; Cl 12.88. Analytical HPLC (Method 3): >97%, $t_r$=23.6 min.

Example 19

1-[N-(Indole-6-carbonyl)-β-(4-morpholinyl)-D-alaninyl]-4-(1-methylpiperidin-4-yl)piperidine Hydrochloride

Prepared from 1-[β-(4-morpholinyl)-D-alaninyl]-4-(1-methylpiperidin-4-yl)piperidine and indole-6-carboxylic acid using methods substantially equivalent to General Coupling Method 1. The HCl salt is prepared following General Salt Formation Method 1.

$^1$H NMR. ES-MS, m/z 482.1 (M+1)$^+$. Analysis For $C_{27}H_{39}N_5O_3 \cdot 1.1$ HCl $\cdot 1.0$ H$_2$O: Calcd: C 60.08; H 7.86; N 12.98; Cl 7.23; Found: C 60.19; H 8.17; N 12.76; Cl 7.11. Analytical HPLC (Method 3): >99%, $t_r$=11.8 min.

Example 20

1-[N-(5-Chloroindole-2-carbonyl)-β-(4-morpholinyl)-D-alaninyl]-4-(1-methylpiperidin-4-yl)piperidine Hydrochloride

Prepared from 1-[β-(4-morpholinyl)-D-alaninyl]-4-(1-methylpiperidin-4-yl)piperidine and 5-chloroindole-2-carboxylic acid using methods substantially equivalent to General Coupling Method 1. The HCl salt is prepared following General Salt Formation Method 1.

$^1$H NMR. ES-MS, m/z 516.3 (M+1)$^+$. Analysis for $C_{27}H_{38}N_5O_3Cl \cdot 1.1$ HCl $\cdot 2.0$ H$_2$O: Calcd: C 54.76; H 7.34; N 11.83; Cl 12.57; Found: C 54.81; H 6.85; N 11.88; Cl 12.78. Analytical HPLC (Method 3): >94%, $t_r$=15.5 min.

Example 21

1-[N-(3-Chloroindole-6-carbonyl)-β-(4-morpholinyl)-D-alaninyl]-4-(1-methylpiperidin-4-yl)piperidine Hydrochloride

Prepared from 1-[β-(4-morpholinyl)-D-alaninyl]-4-(1-methylpiperidin-4-yl)piperidine and 3-chloroindole-6-carboxylic acid using methods substantially equivalent to General Coupling Method 1. The HCl salt is prepared following General Salt Formation Method 1.

$^1$H NMR. ES-MS, m/z 516.3 (M+1)$^+$. Analysis For $C_{27}H_{38}N_5O_3Cl \cdot 1.0$ HCl $\cdot 1.8$ H$_2$O: Calcd: C 55.44; H 7.34; N 11.97; Cl 12.12. Found: C 55.38; H 6.95; N 11.92; Cl 12.30. Analytical HPLC (Method 3): >96%, $t_r$=13.4 min.

Example 22

1-[N-(6-Chlorobenzo[b]thiophene-2-carbonyl)-β-(4-morpholinyl)-D-alaninyl]-4-(1-methylpiperidin-4-yl)piperidine Hydrochloride

Prepared from 1-[β-(4-morpholinyl)-D-alaninyl]-4-(1-methylpiperidin-4-yl)piperidine and 6-chlorobenzo[b]thiophene-2-carboxylic acid using methods substantially equivalent to General Coupling Method 1. The HCl salt is prepared following General Salt Formation Method 1.

$^1$H NMR. ES-MS, m/z 533.3 (M+1)$^+$. Analysis for $C_{27}H_{37}N_4O_3SCl \cdot 1.5$ HCl $\cdot 1.3$ H$_2$O: Calcd: C 53.05; H 6.78; N 9.17; Cl 14.50. Found: C 52.99; H 6.31; N 8.97; Cl 14.54. Analytical HPLC (Method 3): >96%, $t_r$=16.6 min.

Example 23

1-[N-(Indole-6-carbonyl)-β-dimethylamino-D-alaninyl]-4-(1-methylpiperidin-4-yl)piperidine Hydrochloride

Prepared from 1-[β-dimethylamino-D-alaninyl]-4-(1-methylpiperidin-4-yl)piperidine and indole-6-carboxylic acid using methods substantially equivalent to General Coupling Method 1. The HCl salt is prepared following General Salt Formation Method 1.

$^1$H NMR. ES-MS, m/z 440.3 (M+1)$^+$. Analysis For $C_{25}H_{37}N_5O_2 \cdot 1.0$ HCl $\cdot 2.2$ H$_2$O: Calcd: C 58.23; H 8.29; N 13.58; Found: C 58.19; H 8.06; N 13.52. Analytical HPLC (Method 3): >99%, $t_r$=9.5 min.

Example 24

1-[N-(5-Chloroindole-2-carbonyl)-β-dimethylamino-D-alaninyl]-4-(1-methylpiperidin-4-yl)piperidine Hydrochloride

Prepared from 1-[β-dimethylamino-D-alaninyl]-4-(1-methylpiperidin-4-yl)piperidine and 5-chloroindole-2-carboxylic acid using methods substantially equivalent to General Coupling Method 1. The HCl salt is prepared following General Salt Formation Method 1.

$^1$H NMR. ES-MS, m/z 474.3 (M+1)$^+$. Analysis for $C_{25}H_{36}N_5O_2Cl \cdot 1.2$ HCl $\cdot 1.7$ H$_2$O: Calcd: C 54.75; H 7.46; N 12.77; Found: C 55.01; H 7.07; N 12.40. Analytical HPLC (Method 3): >98%, $t_r$=15.8 min.

Example 25

1-[N-(6-Chlorobenzo]b[thiophene-2-carbonyl)-β-dimethylamino-D-alaninyl]-4-(1-methylpiperidin-4-yl)piperidine Hydrochloride Prepared from 1-[β-dimethylamino-D-alaninyl]-4-(1-methylpiperidin-4-yl)piperidine and 6-chlorobenzo[b]thiophene-2-carboxylic acid using methods substantially equivalent to General Coupling Method 1. The HCl salt is prepared following General Salt Formation Method 1.

$^1$H NMR. ES-MS, m/z 491.2 (M+1)$^+$. Analysis For $C_{25}H_{35}N_4O_2SCl.1.2$ HCl.1.5 $H_2O$: Calcd: C 53.44; H 7.03; N 9.97; Found: C 53.20; H 6.64; N 9.80. Analytical HPLC (Method 3): >99%, $t_r$=16.7 min.

Example 26

1-[N-(5-Chloroindole-2-carbonyl)-β-(1-imidazolyl)-D-alaninyl]-4-(1-methylpiperidin-4-yl)piperidine Trihydrochloride Prepared from 1-[β-(1-imidazolyl)-D-alaninyl]-4-(1-methylpiperidin-4-yl)piperidine and 5-chloroindole-2-carboxylic acid using methods substantially equivalent to General Coupling Method 1. Purification by the reverse phase chromatography option gives the hydrochloride salt.

$^1$H NMR. ES-MS, m/z 497.2 (M+1)$^+$. Analysis for $C_{26}H_{33}N_6O_2Cl.3.0$ HCl.1.0 $H_2O$: Calcd: C 50.01; H 6.13; N 13.46; Found: C 49.64; H 5.75; N 12.24. Analytical HPLC (Method 3): >99%, $t_r$=16.1 min.

Example 27

1-[N-(6-Chlorobenzo[b]thiophene-2-carbonyl)-β-(1-imidazol-yl)-D-alaninyl]-4-(1-methylpiperidin-4-yl)piperidine Dihydrochloride Prepared from 1-([β-(1-imidazolyl)-D-alaninyl]-4-(1-methylpiperidin-4-yl)piperidine and 6-chlorobenzo[b]thiophene-2-carboxylic acid using methods substantially equivalent to General Coupling Method 1. Purification by the reverse phase chromatography option gives the hydrochloride salt.

$^1$H NMR. ES-MS, m/z 514.2 (M+1)$^+$. Analysis for $C_{26}H_{32}N_5O_2SCl.2.0$ HCl.3.3 $H_2O$: Calcd: C 48.31; H 6.33; N 10.83; Found: C 48.51; H 5.94; N 10.15. Analytical HPLC (Method 3): >99%, $t_r$=17.0 min.

Example 28

1-[N-(5-Chloroindole-2-carbonyl)-β-(1-piperidinyl)-D-alaninyl]-4-(1-methylpiperidin-4-yl)piperidine Dihydrochloride Prepared from 1-[β-(1-piperidinyl)-D-alaninyl]-4-(1-methylpiperidin-4-yl)piperidine and 5-chloroindole-2-carboxylic acid using methods substantially equivalent to General Coupling Method 1. Purification by the reverse phase chromatography option gives the dihydrochloride salt.

$^1$H NMR. ES-MS, m/z 514.3 (M+1)$^+$. Analysis for $C_{28}H_{40}N_5O_2Cl.2.1$ HCl.5.0 $H_2O$: Calcd: C 49.40; H 7.71; N 10.29; Found: C 49.74; H 7.59; N 9.59. Analytical HPLC (Method 3): >99%, $t_r$=17.0 min.

Example 29

1-[N-(6-Chlorobenzo[b]thiophene-2-carbonyl)-β-(1-piperidinyl)-D-alaninyl]-4-(1-methylpiperidin-4-yl) piperidine Hydrochloride Prepared from 1-[β-(1-piperidinyl)-D-alaninyl]-4-(1-methylpiperidin-4-yl)piperidine and 6-chlorobenzo[b]thiophene-2-carboxylic acid using methods substantially equivalent to General Coupling Method 1. The HCl salt is prepared following General Salt Formation Method 1.

$^1$H NMR. ES-MS, m/z 531.3 (M+1)$^+$. Analysis for $C_{28}H_{39}N_4O_2SCl.1.0$ HCl.0.9 $H_2O$: Calcd: C 57.60; H 7.22; N 9.60; Found: C 57.56; H 7.02; N 9.41. Analytical HPLC (Method 3): >99%, $t_r$=18.5 min.

Preparation of Compounds of Formula (IX), $X^1$=N

1-(N-Boc-D-allo-Threoninyl)-4-(1-methylpiperidin-4-yl)-piperazine

Prepared from N-Boc-D-allo-threonine and 1-(1-methylpiperidin-4-yl)piperazine using methods substantially equivalent to General Coupling Method 1. $^1$H NMR. ES-MS, m/z 385.5 (M+1)$^+$. Analysis For $C_{19}H_{36}N_4O_4.1.0$ $H_2O$: Calcd: C 56.69; H 9.52; N 13.92; Found: C 57.18; H 9.59; N 13.85.

1-(N-Boc-O-Methyl-D-allo-threoninyl)-4-(1-methylpiperidin-4-yl)piperazine

Prepared from N-Boc-O-methyl-D-allo-threonine and 1-(1-methylpiperidin-4-yl)piperazine using methods substantially equivalent to General Coupling Method 1.

$^1$H NMR. ES-MS, m/z 398.8 (M+1)$^+$.

1-(N-Boc-D-Serinyl)-4-(1-methylpiperidin-4-yl) piperazine

Prepared from N-Boc-D-serine and 1-(1-methylpiperidin-4-yl)piperazine using methods substantially equivalent to General Coupling Method 1.

$^1$H NMR. ES-MS, m/z 371.2 (M+1)$^+$. Analysis For $C_{18}H_{34}N_4O_4.0.2$ $H_2O$: Calcd: C 56.88; H 9.02; N 14.74; Found: C 57.02; H 9.05; N 14.43.

1-(N-Boc-D-Methioninyl)-4-(1-methylpiperidin-4-yl)-piperazine

Prepared from N-Boc-D-methionine and 1-(1-methyl-piperidin-4-yl)piperazine using methods substantially equivalent to General Coupling 4.

ES-MS, m/z 415.3 (M+1)$^+$.

1-(N-Boc-β-(4-Morpholinyl)-D-alaninyl]-4-(1-methylpiperidin-4-yl)piperazine

Prepared from N-Boc-β-(4-morpholinyl)-D-alanine potassium salt and 1-(1-methylpiperidin-4-yl)piperazine using methods substantially equivalent to General Coupling Method 1. N-Boc-β-(1-morpholinyl)-D-alanine potassium salt is prepared from Boc-D-serine β-lactone and N-trimethyl-silylmorpholine using methods substantially equivalent to General Lactone Opening Method 2.

$^1$H NMR. ES-MS, m/z 440.3 (M+1)$^+$.

1-[N-Boc-β-(1-Piperidinyl)-D-alaninyl]-4-(1-methylpiperidin-4-yl)piperazine

Prepared from N-Boc-β-(1-piperidinyl)-D-alanine potassium salt and 1-(1-methylpiperidin-4-yl)piperazine using methods substantially equivalent to General Coupling Method 1. N-Boc-β-(1-piperidinyl)-D-alanine potassium salt is prepared from Boc-D-serine β-lactone and 1-(trimethyl-silyl)piperidine using methods substantially equivalent to General Lactone Opening Method 2.

$^1$H NMR. ES-MS, m/z 438.3 (M+1)$^+$.

Preparation of Compounds of Formula (IV), $X^1$=N

1-(D-allo-Threoninyl)-4-(1-methylpiperidin-4-yl)piperazine Hydrochloride

Prepared from 1-(N-Boc-D-allo-threoninyl)-4-(1-methylpiperidin-4-yl)piperazine using methods substantially equivalent to those described in General Deprotection Method 2.

$^1$H NMR. ES-MS, m/z 285.4 (M+1)$^+$.

Analysis for $C_{14}H_{28}N_4O_2 \cdot 3.0$ HCl: Calcd: C 42.70; H 7.94; N 14.23; Cl 27.01; Found: C 42.29; H 7.84; N 14.26; Cl 26.84.

1-(O-Methyl-D-allo-threoninyl)-4-(1-methylpiperidin-4-yl)-piperazine Hydrochloride Prepared from 1-(N-Boc-O-methyl-D-allo-threoninyl)-4-(1-methylpiperidin-4-yl)piperazine using methods substantially equivalent to those described in General Deprotection Method 2.

$^1$H NMR. ES-MS, 299.4 m/z (M+1)$^+$.

1-(D-Serinyl)-4-(1-methylpiperidin-4-yl)piperazine Hydrochloride

Prepared from 1-(N-Boc-D-serinyl)-4-(1-methylpiperidin-4-yl)piperazine using methods substantially equivalent to those described in General Deprotection Method 2.

$^1$H NMR. ES-MS, m/z 271.4 (M+1)$^+$. Analysis For $C_{13}H_{26}N_4O_2 \cdot 3.0$ HCl$\cdot 1.0$ H$_2$O: Calcd: C 39.25; H 7.86; N 14.09; Cl 26.74; Found: C 39.69; H 7.52; N 14.25; Cl 27.35.

1-(D-Methioninyl)-4-(1-methylpiperidin-4-yl)piperazine

Prepared from 1-(N-Boc-D-methioninyl)-4-(1-methylpiperidin-4-yl)piperazine using methods substantially equivalent to those described in General Deprotection Method 1.

ES-MS, m/z 315.2 (M+1)$^+$.

1-[β-(4-Morpholinyl)-D-alaninyl]-4-(1-methylpiperidin-4-yl)-piperazine Hydrochloride Prepared from 1-[N-Boc-β-(4-morpholinyl)-D-alaninyl]-4-(1-methylpiperidin-4-yl)piperazine using methods substantially equivalent to those described in General Deprotection Method 2.

$^1$H NMR. ES-MS, m/z 340.3 (M+1)$^+$.

1-[β-(1-Piperidinyl)-D-alaninyl]-4-(1-methylpiperidin-4-yl)-piperazine Hydrochloride Prepared from 1-[N-Boc-β-(1-piperidinyl)-D-alaninyl]-4-(1-methylpiperidin-4-yl)piperazine using methods substantially equivalent to those described in General Deprotection Method 2.

$^1$H NMR. ES-MS, m/z 338.3 (M+1)$^+$.

Examples, $X^1$=N

Example 30

1-[N-(6-Chlorobenzo[b]thiophene-2-carbonyl)-D-allo-threoninyl]-4-(1-methylpiperidin-4-yl)piperazine Hydrochloride Prepared from 1-(D-allo-threoninyl)-4-(1-methylpiperidin-4-yl)piperazine hydrochloride and 6-chlorobenzo[b]thiophene-2-carboxylic acid using methods substantially equivalent to General Coupling Method 1. The final crude product is treated with aqueous 0.2 N HCl and purified via prep-HPLC (80:20 to 40:60 0.01% HCl in water:acetonitrile).

$^1$H NMR. ES-MS, m/z 479.3 (M+1)$^+$; 477.4 (M−1)$^−$. Analysis for $C_{23}H_{31}ClN_4O_3S \cdot 1.1$ HCl$\cdot 3.3$ H$_2$O: Calcd: C 47.74; H 6.74; N 9.68; Found: C 47.31; H 6.01; N 9.66. Analytical HPLC (Method 1): >99%, $t_r$=22.1 min.

Example 31

1-[N-(5-Chloroindole-2-carbonyl)-D-allo-threoninyl]-4-(1-methylpiperidin-4-yl)piperazine Hydrochloride Prepared from 1-(D-allo-threoninyl)-4-(1-methylpiperidin-4-yl)piperazine hydrochloride and 5-chloroindole-2-carboxylic acid using methods substantially equivalent to General Coupling Method 1. The HCl salt is prepared following Salt Formation Method 1. The final crude product is treated with aqueous 0.2 N HCl and purified via prep-HPLC (80:20 to 40:60 0.01% HCl in water:acetonitrile).

$^1$H NMR. ES-MS, m/z 462.2 (M+1)$^+$; 460.2 (M−1)$^−$. Analysis for $C_{23}H_{32}ClN_5O_3 \cdot 1.1$ HCl$\cdot 4.50$ H$_2$O: Calcd: C 47.37; H 7.28; N 12.01; Found: C 47.27; H 6.37; N 11.95. Analytical HPLC (Method 1): >96%, $t_r$=21.0 min.

Example 32

1-[N-(6-Chlorobenzo[b]thiophene-2-carbonyl)-O-methyl-D-allo-threoninyl]-4-(1-methylpiperidin-4-yl)piperazine Hydrochloride Prepared from 1-(O-methyl-D-allo-threoninyl)-4-(1-methylpiperidin-4-yl)piperazine hydrochloride and 6-chlorobenzo[b]thiophene-2-carboxylic acid using methods substantially equivalent to General Coupling Method 1. The HCl salt is prepared following Salt Formation Method 1.

$^1$H NMR. ES-MS, m/z 493.1 (M+1)$^+$; 491.2 (M−1)$^−$. Analysis for $C_{23}H_{31}ClN_4O_3S \cdot 1.0$ HCl$\cdot 1.0$ H$_2$O: Calcd: C 51.78; H 6.42; N 10.50; Found: C 51.93; H 7.02; N 10.28. Analytical HPLC (Method 1): >96%, $t_r$=22.8 min.

Example 33

1-[N-(5-Chloroindole-2-carbonyl)-O-methyl-D-allo-threoninyl]-4-(1-methylpiperidin-4-yl)piperazine Hydrochloride Prepared from 1-(O-methyl-D-allo-threoninyl)-4-(1-methylpiperidin-4-yl)piperazine hydrochloride and 5-chloroindole-2-carboxylic acid using methods substantially equivalent to General Coupling Method 1. The HCl salt is prepared following Salt Formation Method 1.
$^1$H NMR. ES-MS, m/z 476.1 (M+1)$^+$; 474.2 (M–1)$^-$. Analytical HPLC (Method 1): >96%, $t_r$=21.4 min.

Example 34

1-[N-(6-Chlorobenzo[b]thiophene-2-carbonyl)-D-serinyl-4-(1-methylpiperidin-4-yl)piperazine Hydrochloride Prepared from 1-(D-serinyl)-4-(1-methylpiperidin-4-yl)piperazine hydrochloride and 6-chlorobenzo[b]thiophene-2-carboxylic acid using methods substantially equivalent to General Coupling Method 1. The HCl salt is prepared following Salt Formation Method 1.
$^1$H NMR. ES-MS, m/z 465.1 (M+1)$^+$; 463.1 (M–1)$^-$. Analysis for $C_{22}H_{29}ClN_4O_2S.1.3$ HCl.3.3 $H_2O$: Calcd: C 49.26; H 6.93; N 10.45; Found: C 48.98; H 6.27; N 10.72. Analytical HPLC (Method 1): >99%, $t_r$=18.9 min.

Example 35

1-[N-(5-Chloroindole-2-carbonyl)-D-serinyl]-4-(1-methylpiperidin-4-yl)piperazine Hydrochloride Prepared from 1-(D-serinyl)-4-(1-methylpiperidin-4-yl)piperazine hydrochloride and 5-chloroindole-2-carboxylic acid using methods substantially equivalent to General Coupling Method 1. The HCl salt is prepared following Salt Formation Method 1.
$^1$H NMR. ES-MS, m/z 448.2(M+1)$^+$; 446.2(M–1)$^-$. Analysis For $C_{22}H_{30}ClN_5O_2$.1.1 HCl.3.0 $H_2O$ Calcd: C 47.74; H 6.90; N 12.92; Found: C 48.47; H 6.18; N 12.70. Analytical HPLC (Method 1): >99%, $t_r$=18.9 min.

Example 36

1-[N-(Indole-6-carbonyl)-D-serinyl]-4-(1-methylpiperidin-4-yl)piperazine Hydrochloride Prepared from 1-(D-serinyl)-4-(1-methylpiperidin-4-yl)piperazine hydrochloride and indole-6-carboxylic acid using methods substantially equivalent to General Coupling Method 1. The HCl salt is prepared following General Salt Formation Method 1.
$^1$H NMR. ES-MS, m/z 448.2 (M+1)$^+$; 446.2 (M–1)$^-$. Analysis for $C_{22}H_{30}ClN_5O_3$.1.1 HCl.3.0 $H_2O$: Calcd: C 48.74; H 6.91; N 12.98; Found: C 48.47; H 6.18; N 12.70. Analytical HPLC (Method 1): >99%, $t_r$=18.9 min.

Example 37

1-[N-(4-Methoxybenzoyl)-D-methioninyl]-4-(1-methylpiperidin-4-yl)piperazine Hydrochloride Prepared from 1-(D-methioninyl)-4-(1-methylpiperidin-4-yl)piperazine hydrochloride and 4-methoxybenzoic acid using methods substantially equivalent to General Coupling Method 4. The HCl salt is prepared following General Salt Formation Method 2.
$^1$H NMR. ES-MS, m/z 449.2 (M+1)$^+$. Analysis for $C_{23}H_{36}N_4O_3$.1.8 HCl.1.2 $H_2O$: Calcd: C 51.55; H 7.56; N 10.45; Cl 11.91; Found: C 51.23; H 7.28; N 10.16; Cl 12.39. Analytical HPLC (Method 1): 98%, $t_r$=14.4 min.

Example 38

1-[N-(Indole-6-carbonyl)-D-methioninyl]-4-(1-methylpiperidin-4-yl)piperazine Hydrochloride Prepared from 1-(D-methioninyl)-4-(1-methylpiperidin-4-yl)piperazine hydrochloride and 6-indole carboxylic acid using methods substantially equivalent to General Coupling Method 4. The HCl salt is prepared following General Salt Formation Method 2.
$^1$H NMR. ES-MS, m/z 449.2 (M+1)$^+$. Analysis for $C_{23}H_{36}N_4O_3$.1.8 HCl.1.2 $H_2O$: Calcd: C 51.55; H 7.56; N 10.45; Cl 11.91; Found: C 51.23; H 7.28; N 10.16; Cl 12.39. Analytical HPLC (Method 1): 98%, $t_r$=14.4 min.

Example 39

1-[N-(Indole-6-carbonyl)-β-(4-morpholinyl)-D-alaninyl]-4-(1-methylpiperidin-4-yl)piperazine Hydrochloride Prepared from 1-[β-(4-morpholinyl)-D-alaninyl]-4-(1-methylpiperidin-4-yl)piperazine and indole-6-carboxylic acid using methods substantially equivalent to General Coupling Method 1. The HCl salt is prepared following General Salt Formation Method 1.
$^1$H NMR. ES-MS, m/z 483.3 (M+1)$^+$. Analysis for $C_{26}H_{38}N_6O_3$.1.6 HCl.1.3 $H_2O$: Calcd: C 55.33; H 7.54; N 14.89; Found: C 55.38; H 7.15; N 14.98. Analytical HPLC (Method 3): >99%, $t_r$=11.7 min.

Example 40

1-[N-(5-Chloroindole-2-carbonyl)-β-(4-morpholinyl)-D-alaninyl]-4-(1-methylpiperidin-4-yl)piperazine Hydrochloride Prepared from 1-[β-(4-morpholinyl)-D-alaninyl]-4-(1-methylpiperidin-4-yl)piperazine and 5-chloroindole-2-carboxylic acid using methods substantially equivalent to General Coupling Method 1. The HCl salt is prepared following General Salt Formation Method 1.
$^1$H NMR. ES-MS, m/z 517.3 (M+1)$^+$. Analysis for $C_{26}H_{37}N_6O_3Cl$.1.0 HCl.1.5 $H_2O$: Calcd: C 53.79; H 7.12; N 14.48. Found: C 53.52; H 6.89; N 14.18. Analytical HPLC (Method 3): >99%, $t_r$=10.7 min.

Example 41

1-[N-(6-Chlorobenzo[b]thiophene-2-carbonyl)-β-(4-morpholinyl)-D-alaninyl]-4-(1-methylpiperidin-4-yl)piperazine Hydrochloride Prepared from 1-[β-(4-morpholinyl)-D-alaninyl]-4-(1-methylpiperidin-4-yl) piperazine and 6-chlorobenzo[b]thiophene-2-carboxylic acid using methods substantially equivalent to General Coupling Method 1. The HCl salt is prepared following General Salt Formation Method 1.

$^1$H NMR. ES-MS, m/z 534.2 (M+1)$^+$. Analysis for C$_{26}$H$_{36}$N$_5$O$_3$SCl.1.0 HCl.1.7 H$_2$O: Calcd: C 51.94; H 6.77; N 11.65; Found: C 51.98; H 6.58; N 11.62. Analytical HPLC (Method 3): >99%, t$_r$=12.7 min.

Example 42

1-[N-(5-Chloroindole-2-carbonyl)-β-(1-piperidinyl)-D-alaninyl]-4-(1-methylpiperidin-4-yl)piperazine Hydrochloride Prepared from 1-[β-(1-piperidinyl)-D-alaninyl]-4-(1-methylpiperidin-4-yl)piperazine and 5-chloroindole-2-carboxylic acid using methods substantially equivalent to General Coupling Method 1. Purification by the reverse phase chromatography option gives the hydrochloride salt.

$^1$H NMR. ES-MS, m/z 515.3 (M+1)$^+$. Analysis for C$_{27}$H$_{39}$N$_6$O$_2$Cl.3.3 HCl.1.8 H$_2$O: Calcd: C 48.56; H 6.93; N 12.58. Found: C 48.50; H 6.55; N 11.58. Analytical HPLC (Method 3): >97%, t$_r$=12.8 min.

Example 43

1-[N-(6-Chlorobenzo[b]thiophene-2-carbonyl)-β-(1-piperidinyl)-D-alaninyl]-4-(1-methylpiperidin-4-yl) piperazine Hydrochloride Prepared from 1-[β-(1-piperidinyl)-D-alaninyl]-4-(1-methylpiperidin-4-yl) piperazine and 6-chlorobenzo[b] thiophene-2-carboxylic acid using methods substantially equivalent to General Coupling Method 1. The HCl salt is prepared following General Salt Formation Method 1.

$^1$H NMR. ES-MS, m/z 532.3 (M+1)$^+$. Analysis For C$_{27}$H$_{38}$N$_5$O$_2$SCl.1.0 HCl.1.8 H$_2$O: Calcd: C 53.95; H 7.14; N 11.65; Found: C 54.11; H 6.90; N 11.26. Analytical HPLC (Method 3): >99%, t$_r$=14.5 min.

Enzyme Inhibition Assays

The ability of a test compound to inhibit factor Xa may be evaluated in one or more of the following Enzyme Inhibition assays, or in other standard assays known to those skilled in the art.

Enzyme Inhibition Assay

Human factor Xa and human thrombin are purchased from Enzyme Research Laboratories (South Bend, Ind., USA). Other proteases are from other commercial sources. Chromogenic para-nitroanilide peptide protease substrates are purchased from Midwest Biotech (Fishers, Ind., USA).

The binding affinities for human factor Xa are measured as apparent association constants (Kass) derived from protease inhibition kinetics as described previously.[a,b,c,d] The apparent Kass values are obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol is: 50 μL buffer (0.06 M tris, 0.3 M NaCl, pH, 7.4); 25 μL inhibitor test solution (in MeOH); 25 μL human factor Xa (32 nM in 0.03 M tris, 0.15 M NaCl, 1 mg/mL HSA); finally, 150 μL BzIleGluGlyArgpNA (0.3 mM in water) added within min to start hydrolysis. Final [factor Xa] is 3.2 nM. [Free Xa] and [bound Xa] are determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent Kass=[E:I]/[E$_f$][I$_f$]=[E$_b$]/[E$_f$][I$^o$−I$_b$]. The apparent Kass values so obtained are approximately the inverse of the Ki for the respective inhibitors [1/appKass=app Ki]. The variability of mean apparent Kass values determined at the single substrate concentration is +/−15%. The assay system Km was measured as 0.347+/−0.031 mM [n=4]; and Vmax was 13.11+/−0.76 μM/min.

Kass values are determined with thrombin and other proteases using the same protocol with the following enzyme and substrate concentrations:
thrombin, 5.9 nM with 0.2 mM BzPheValArgpNA;
factor XIa, 1.2 nM with 0.4 mM pyroGluProArgpNA;
factor XIIa, 10 nM with 0.2 mM HDProPheArgpNA;
plasmin, 3.4 nM with 0.5 mM HDValLeuLyspNA;
nt-PA, 1.2 nM with 0.8 mM HDIleProArgpNA;
urokinase, 0.4 nM with 0.4 mM pyroGluGlyArgpNA;
aPC, 3 nM with 0.174 mM pyroGluProArgpNA;
plasma kallikrein, 1.9 nM with D-ProPheArgpNA; and
bovine trypsin, 1.4 nM with 0.18 mM BzPheValArgpNA.

CITATIONS (a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-C B Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489-3493 (1997).

(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173-183 (1996).

(c) Smith G F, D S Gifford-Moore, T J Craft, N Chirgadze, K J Ruterbories, T D Lindstrom, J H Satterwhite. Efegatran: A New Cardiovascular Anticosagulant. In New Anticoagulants for the Cardiovascular Patient. Ed. R Pifarre. Hanley & Belfus, Inc., Philadelphia (1997) pp 265-300.

(d) Sall D J, D L Bailey, J A Bastian, N Y Chirgadze, A C Clemens-Smith, M L Denney, M J Fisher, D D Geira, D S Gifford-Moore, R W Harper, L M Johnson, V J Klimkowski, T J Kohn, H S Lin, J R McCowan, A D Palkowitz, M E Richett, G F Smith, D W Snyder, K Takeuchi, J E Toth, M Zang. Diamino Benzo[b]thiophene Derivatives as a Novel Class of Active Site Directed Thrombin Inhibitors: 5. Potency, Efficacy and Pharmacokinetic Properties of Modified C-3 Side Chain Derivatives. J. Med. Chem., 43, 649-663 (2000).

The compounds of formula (I) exemplified herein have been found to exhibit a Kass of greater than 1×10$^6$ L/mole in the enzyme inhibition assay. For example, the compounds, or their pharmaceutically acceptable salts, exemplified herein have been to exhibit Kass values of greater than 1×10$^6$ L/mole.

The ability of a test compound to elongate Partial Thromboplastin Time (Prothrombin Time) may be evaluated in the following test protocols.

Partial Thromboplastin Time (Prothrombin) Test Protocol

Venous blood is collected into 3.2% (0.109 M) trisodium citrate vacutainer tubes at 1 volume of anticoagulant to nine volumes of blood. The blood cells are separated by centrifugation at 700 g for ten minutes to yield plasma, which is frozen at 70° C. until required.

To perform the test, 100 μL of plasma are pipetted into in a glass test tube, 1 μL of test compound in DMSO is added, and allowed to warm to 37° over two minutes. 100 μL of warm (37°) Manchester (tissue thromboplastin) reagent (Helena Biosciences, UK) is added, allowed to equilibrate for two minutes. 100 μL of warm (37°) 25 mM calcium chloride solution is added to initiate clotting. The test tube is tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

Compounds of the invention have been found to significantly elongate the partial thromboplastin time (Prothrombin time).

Alternative Prothrombin Time and APTT Protocols

Coagulation Determinations: Prothrombin Times and APTT values are determined in HUMAN PLASMA with a STA instrument (Stago). BioPT is a special non-plasma clotting assay triggered with human tissue factor (Innovin). Possible binding to albumen or to lipid are assessed by comparing the BioPT effects in the presence/absence of 30 mg/mL human albumen (HSA) and 1 mg/mL phosphatidyl choline (PC). Inhibitors are delivered in 50% aqueous methanol vehicle.

APTT ASSAY

75 μL plasma Citrol Baxter-Dade Citrated Normal Human Plasma
25 μL test solution
75 μL Actin Baxter-Dade Activated Cephaloplastin incubate 2 min min. @ 37 ° C.
75 μl CaCl₂ (0.02 M)

PT ASSAY

75 μL plasma
25 μL test solution
75 μL saline incubate 1 min. @ 37° C.
75 μL Innovin Baxter-Dade Recombinant Human Tissue Factor

The invention claimed is:
1. A compound of formula (I)

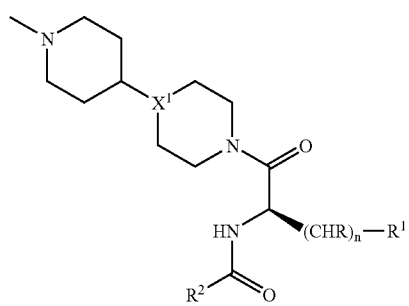

in which
X¹ represents N;
n is 1 or 2;
each R represents hydrogen or methyl;
R¹ represents imidazol-1-yl or $X^a R^a$
in which
$X^a$ represents O, S or $NR^b$;
$R^a$ represents a hydrogen atom, a (1-4C)alkyl group, a phenyl group or a pyridyl group;
$R^b$ represents a hydrogen atom, a (1-4C)alkyl group or, together with $R^a$ and the nitrogen atom to which they are attached represents a saturated 4 to 6-membered ring which may contain, as a ring member, one of O, S and $NR^c$ in which $R^c$ represents hydrogen or (1-4C) alkyl; and
R² is selected from

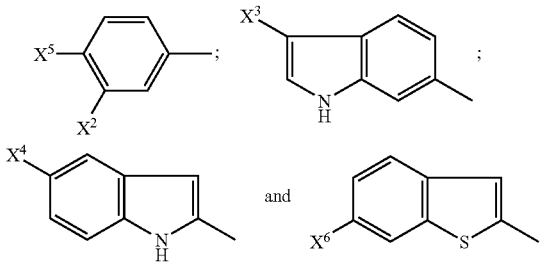

in which
X² represents a hydrogen atom, a halogen atom or an amino group;
X³ represents a hydrogen atom, a methyl group, a fluorine atom, a chlorine atom or a bromine atom;
X⁴ represents a hydrogen atom, a methyl group or a halogen atom;
X⁵ represents a chlorine atom, a methoxy group or a methyl group; and
X⁶ represents a hydrogen atom, a halogen atom or a methyl group;
or a pharmaceutically acceptable salt thereof.

2. A compound as claimed in claim 1, in which (CHR)ₙ is selected from CH₂, CHCH₃ and CH₂CH₂.

3. A compound as claimed in claim 2, in which R¹ represents imidazol-1-yl, hydroxy, (1-4C)alkoxy, (1-4C)alkylthio, di(1-4C)alkylamino, phenylthio, pyridylthio, piperidin-1-yl or morpholino.

4. A compound as claimed in claim 3, in which R¹ represents imidazol-1-yl, hydroxy, methoxy, methylthio, 2-propylthio, dimethylamino, phenylthio, pyrid-2-ylthio, piperidin-1-yl or morpholino.

5. A compound as claimed in claim 4, in which (CHR)ₙR₁ represents imidazol-1-ylmethyl, hydroxymethyl, 1-hydroxyethyl, methoxymethyl, 1-methoxyethyl, methylthiomethyl, prop-2-ylthiomethyl, 2-methylthioethyl, N,N-dimethylaminomethyl, phenylthiomethyl, pyrid-2-ylthiomethyl, piperidin-1-ylmethyl or morpholinomethyl.

6. A compound as claimed in any one of claims 1 to 5, in which X² represents a hydrogen atom or a halogen atom.

7. A compound as claimed in claim 6, in which
X² represents a hydrogen atom or a fluorine atom;
X³ represents a hydrogen atom, a fluorine atom, a chlorine atom or a methyl group;
X⁴ represents a chlorine atom;
X⁵ represents a chlorine atom or a methoxy group; and
X⁶ represents a chlorine atom.

8. A compound as claimed in claim 1, in which R² is 4-chlorophenyl, 4-methoxyphenyl, 3-fluoro-4-methoxyphenyl, indol-6-yl, 3-methylindol-6-yl, 3-chloroindol-6-yl, 5-fluoroindol-2-yl, 5-chloroindol-2-yl or 6-chlorobenzo[b]thiophen-2-yl.

9. A compound as claimed in claim 8, in which R² is 4-methoxyphenyl, indol-6-yl or 5-chloroindol-2-yl.

10. A pharmaceutical composition, which comprises a compound as claimed in claim 1, together with a pharmaceutically acceptable diluent or carrier.

11. A process for preparing a compound as claimed in claim 1, which comprises (a) reacting a compound of formula (II)

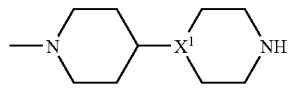
(II)

or a salt thereof, with a compound of formula (III)

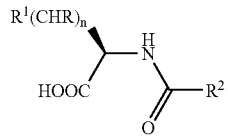
(III)

or a reactive derivative thereof; or (b) reacting a compound of formula (IV)

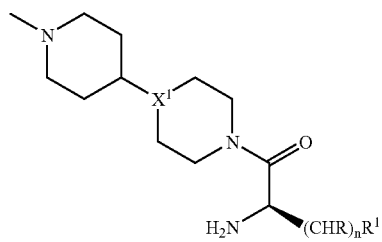
(IV)

or a salt thereof, with a compound of formula (V)

(V)

or a salt or reactive derivative thereof;
followed, if a pharmaceutically acceptable salt is desired, by forming a pharmaceutically acceptable salt.

12. A compound of formula (IV)

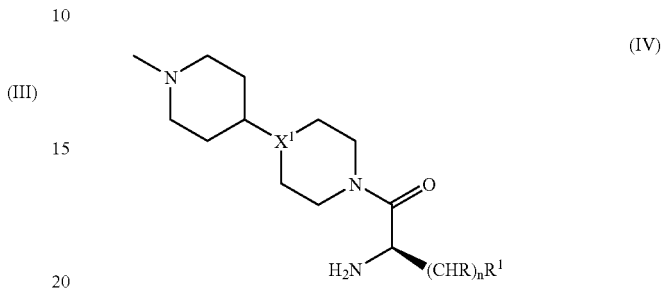
(IV)

or a salt thereof, in which $X^1$ represents CH or N; and n, R and $R^1$ are as defined in claim 1.

13. A method of treating a thrombotic disorder selected from venous thrombosis, pulmonary embolism, arterial thrombosis, myocardial ischaemia, myocardial infarction and cerebral thrombosis in a subject requiring treatment, which comprises administering an effective amount of a compound as claimed in claim 1.

* * * * *